United States Patent
Bosque et al.

Patent Number: 5,830,135
Date of Patent: Nov. 3, 1998

[54] FUZZY LOGIC ALARM SYSTEM FOR PULSE OXIMETERS

[76] Inventors: Elena M. Bosque, 2355 Beach Blvd.#301, Pacifica, Calif. 94044; William Siler, 1901 Hoke Ave., Birmingham, Ala. 35217; Steven L. Goldman, 20 Underhill Rd., Mill Valley, Calif. 94941

[21] Appl. No.: 220,544

[22] Filed: Mar. 31, 1994

[51] Int. Cl.$^6$ .................................................. A61B 5/00
[52] U.S. Cl. ........................... 600/323; 356/41; 600/473; 600/476
[58] Field of Search ........................... 128/633–4, 664–7; 356/39–41

[56] References Cited

U.S. PATENT DOCUMENTS

| | | |
|---|---|---|
| 3,638,640 | 2/1972 | Shaw . |
| 4,167,331 | 9/1979 | Nielsen ..................................... 356/39 |
| 4,407,290 | 10/1983 | Wilber ..................................... 128/633 |
| 4,453,218 | 6/1984 | Sperinde et al. ........................ 364/416 |
| 4,800,495 | 1/1989 | Smith ................................ 364/413.03 |
| 5,339,818 | 8/1994 | Baker et al. ............................. 128/677 |
| 5,355,880 | 10/1994 | Thomas et al. .......................... 128/633 |
| 5,368,224 | 11/1994 | Richardson et al. .................... 128/633 |
| 5,385,143 | 1/1995 | Aoyagi .................................... 128/633 |
| 5,494,032 | 2/1996 | Robinson et al. ....................... 128/633 |

OTHER PUBLICATIONS

Ying, Hao, Ph.D., "An expert system–shell–based fuzzy controller: Theory, development, and application to the control of postsurgical hypertension", A Dissertation of Alabama, 1990.

*PC Computing Magazine*— Robert Haavind, "Fuzzy Logic", Aug. 1989, pp. 147–149.

*AI Expert Magazine*— Tom J. Schwartz, "Fuzzy Systems in the Real World" Aug. 1990, pp. 29–36.

*Report From the Pacific Edge*— Donald S. Fitch, Microskills, "Fuzzy Logic and Quality", Aug. 1990 pp. 1–2.

*Automotive Electronics*— Andrea Saxer, "Nissan Close to Introducing Fuzzy Logic Transmission Controller" pp. 1 and 12.

*Electronic Engineering Times* — R. Colin Johnson "Fuzzy help for expert system", Jul. 23, 1990, pp. 37 & 42.

*Business Domestic*— Takashi Ono, "Everything's fuzzy among household appliances".

*Japan Times* (Cartoons), Leigh & Leigh, "Nihon–zone", Sep. 1, 1990.

*Electronic Engineering Times*— R. Colin Johnson, "Japan sets fuzzy group", Sep. 3, 1990, pp. 18 & 24.

(List continued on next page.)

*Primary Examiner*—Lee S. Cohen
*Assistant Examiner*—Eric F. Winakur
*Attorney, Agent, or Firm*—Dergosits & Noah LLP

[57] ABSTRACT

A new alarm system for pulse oximeters, based on fuzzy logic, will differentiate false alarms, caused by artifact, from true alarms. Numeric input variables and corresponding fuzzy sets (oxygen saturation HIGH (high O2), NO (normal O2) and YES (desaturation) and rate of change of oxygen saturation (HIGH, MEDIUM and LOW) and their membership functions are defined. An output fuzzy set ARTIFACT is defined. Input voltages from the pulse oximeter are sampled and converted to digital form. The sampled voltages are converted by the membership functions into confidences that each fuzzy set descriptor for oxygen desaturation and reate of change apply. Rules are specified which result in confidences that the fuzzy set descriptors for ARTIFACT apply. Further rules govern the issuance of alarms for oxygen desaturation or for artifacts, momentary or continuous, so that the nurse can take appropriate action. The fuzzy logic alarm system program is written in Quick Basic 4.5, by Microsoft (R). The advantage of using the fuzzy logic alarm system for a pulse oximeter used in infants is that there will be at least 34% fewer false alarms. Pulse oximeter alarms which better reflect the actual situation will improve the specificity of the alarm system and may decrease the potential "Cry Wolf" response of the caretaker, which now exists.

16 Claims, 10 Drawing Sheets

OTHER PUBLICATIONS

*IEEE Spectrum*— Paul Wallich, "Software 'doctor' prescribes remedies", Oct. 1986, pp. 43–48.
*Technology*— Don Clark, "Sony Enters Hand–Held Computer Field", Mar. 8, 1990, 2 pages.

Elena Marie Bosque "Symbiosis of Nurse and Machine Through Fuzzy Logic: Improved Specificity of a New Neonatal Pulse Oximeter Alarm", ©1992.

Fig. 1

Membership Functions for Fuzzy Set of "Oxygen Saturation"

Fig. 2A
Computer Program Listing

Program BOSQUE (source code BOSQUE. BAS, executable module BOSQUE. EXE) is a preliminary fuzzy alarm system for a neonatal pulse oximeter.

The program may be simply executed by entering (at the DOS prompt)
 bosque < ting.inp (wangfeng.inp, gonzalez,inp)

although this redirection of the input makes it impossible to use the end-of-frame options described below.

Normal input, on entering BOSQUE at the DOS prompt, is:

DATA FILE (ting.dat, wangfeng.dat or gonzalez.dat)
SAMPLE POINTS PER POINTS PROCESSED (permits reducing the sampling rate if desired. I use a value of 1, so that every point is processed.)
SAO2 FOR .5 CONFIDENCE DESATURATION (I use 0.85)
SAO2 FOR CONFIDENCE .5 HIGH O2 (I use .95)
RATE FOR CONFIDENCE 1 MEDIUM (I use 0.05)
RATE FOR CONFIDENCE 1 HIGH (I use 0.5)
RATE SCALE FACTOR FOR PLOT (I use 5)
WEIGHT FOR LAST POINT INPUT (I use 0.1)
LENGTH OF LINE BETWEEN POINTS (I use 1)

Output includes the original SAO2 wave, scaled to read from 0.5 (bottom) to 1.1 (top). Lines are drawn across the screen at SAO2 values of 0.5 (bottom), 0.75 (middle), and 1.0 (toward the top). Also plotted is the rate of change of SAO2, plotted with zero at the 0.5 SAO2 line.

Actions are these:

HIGH O2: Turns traces blue, pulses of sound at 440 Herz.

MOMENTARY ARTIFACT: small circle drawn on SAO2 and RATE traces, short pulse of sound at 256 herz.

CONTINUOUS ARTIFACT: traces blue, sound at 256 Herz.

DESATURATION: traces red, sound alternates between 512 and 602 Herz.

While the program is running, key presses execute some run-time options at the end of a frame. Pressing the P key causes a pause at the end of a frame (Hit any key to continue); the Q key enables quitting the program (Press any key to quit); the H key toggles the sound signal for high O2; the U key increases the level required for high and medium rate fuzzification, making the system less sensitive to artifacts; the D key decreases these levels, making the system more sensitive to artifacts.

If it is desired simply to view the data, run program PLOTIT.

The program language is Quick Basic 4.5, by Microsoft ®.

Fig. 2B
Computer Program Listing

```
REM ROUTINE TOP PLOT BOSQUE GRAPHS
INPUT "Data file"; FILE$
INPUT "Delta X"; DX
INPUT "Break at end of line for key press (Y/N)"; BK$
BK$ = UCASE$ (BK$)

ON ERROR GOTO NOFILE
OPEN FILE$ FOR INPUT AS 1
SCREEN 1
COLOR 0, 1
WINDOW (0,0) - (300, 1.2)

INPUT #1, JUNK, SAO21
ON ERROR GOTO FINISH

FOR K = 0 TO 1000
    CLS
    PRINT "Frame"; K
    REM Tick marks
    FOR X = .1 TO 1.1 STEP .2
        LINE (0, X) - (3, X)
    NEXT X
    FOR X = 0 TO 1.2 STEP .2
        LINE (0, X) - (6, X)
    NEXT X
    FOR I = DX TO 300 STEP DX
        FOR J = 1 TO DX
            INPUT #1, JUNK, SAO22
        NEXT J
        LINE (I - DX, SAO21) - (I, SAO22)
        SAO21 = SAO22
    NEXT I
    IF BK$ = "Y" THEN
        DO: LOOP WHILE INKEY$ = ""
    END IF
NEXT K FINISH:
DO: LOOP WHILE INKEY$ = ""
SCREEN 0
WIDTH 80
PRINT "Plotted"; 300 * K + I; "points."
END
NOFILE:
DO: LOOP WHILE INKEY$ = ""
SCREEN 0
WIDTH 80
PRINT "END OF DATA"
END
```

Fig. 2C
Computer Program Listing

```
REM ROUTINE TO PLOT BOSQUE GRAPHS
REM BOSQUE. BAS
REM 02-13-92 WS

REM Colors: 0 = black, 1 = blue, 2 = red, 3 = white (default)

REM Fuzzy sets:
REM RATE.HIGH, RATE.MEDIUM, RATE.LOW
REM DESAT.YES, DESAT.NO, DESAT.HIGH
REM oldDESAT.YES, oldDESAT.NO
REM ARTIFACT.YES, ARTIFACT.NO
REM oldARTIFACT.YES, oldARTIFACT.NO REM Fuzzy logic operators REM Fuzzy AND

DEF FNFZAND (A, B)
IF A < B THEN C = A ELSE C = B
FNFZAND = C
END DEF

REM Fuzzy OR

DEF FNFZOR (A, B)
IF A > B THEN C = A ELSE C = B
FNFZOR = C
END DEF

REM Fuzzy NOT

DEF FNFZNOT (A)
FNFZNOT = 1 - A
END DEF

REM Input run parameters from keyboard

INPUT "Data file"; FILE$
INPUT "Samples per computed point"; DX
INPUT "SAO2 at 0.5 confidence desaturation YES"; desat
desat = desat * 2 - 1
INPUT "SAO2 AT 0.5 confidence O2 HIGH"; HIGHO2
HIGHO2 = HIGHO2 * 2 - 1
INPUT "Rate at confidence 1 rate MEDIUM"; testRATE.MEDIUM
INPUT "Rate at confidence 1 rate HIGH"; testRATE.HIGH
INPUT "Rate multiplier for plot"; MPY
INPUT "Weight of last sample for moving average (0-1)"; WT
INPUT "Length of line between points in pixels"; PIX
```

Fig. 2D
Computer Program Listing

REM Initialize file, screen

ON ERROR GOTO NOFILE
OPEN FILE$ FOR INPUT AS 1
SCREEN 1
COLOR 0, 1
WINDOW (0, 0) - (300, 1.25)
LINECOLOR = 3

REM Initialize program variables

INPUT #1, JUNK, SAO21
REM OLD moving average
MA1 = SAO21
REM Fuzzy set for artifacts on last point
oldARTIFACT.YES = 0
oldARTIFACT.NO = 1
REM Fuzzy set for desaturation on last point
oldDESAT.YES = 0
oldDESAT.NO = 1
REM numerical value of last rate
RATE1 = 0
REM enables, disables sound warning for high O2
SOUNDHI$ = "Y"

ON ERROR GOTO FINISH

REM Start loop over screen frames

```
FOR FRAME = 0 TO 1000
    PRINT "FRAME"; FRAME
    REM Tick marks
    FOR X = 0 TO 1.21 STEP .1
        LINE (0, X) - (3, X)
    NEXT X
    FOR X = 0 TO 1.21 STEP .2
        LINE (3, X) - (6, X)
    NEXT X
    LINE (6, .5) - (300, .5)
    LINE (6, 1) - (300, 1)

REM Loop over points in a frame

FOR I = PIX TO 300 STEP PIX
            REM Input extra samples (if any) and sample to be used
            FOR J = 1 TO DX
                INPUT #1, JUNK, SAO22
            NEXT J
            REM Plot original data
```

Fig. 2 E
Computer Program Listing

```
LINE (I - PIX, SAO21) - (I, SAO22), LINECOLOR

REM Get moving average
MA2 = (1 - WT) * MA1 = WT * SAO22

REM Plot moving average of SAO2
REM LINE (I - PIX, MA1) - (I, MA2), 2

REM Plot unsmoothed rate
RATE2 = (SAO22 - MA1) / DX
LINE (I - PIX, RATE1 * MPY + .5) - (I, RATE2 * MPY + .5),
      LINECOLOR
REM Get absolute value of RATE2 FOR later tests
ABSRATE = ABS (RATE2)

REM Fuzzify SAO2 into fuzzy set DESAT

REM get desaturation confidence similarly
IF MA2 > 2 * DESAT - 1 THEN
      DESAT.YES = (1 - MA2) / (2 * (1 - desat))
      DESAT.NO = FNFZNOT (DESAT.YES)
ELSE
      DESAT.YES = 1
      DESAT.NO = FNFZNOT (DESAT.YES)
END IF
IF MA2 > 2 * HIGHO2 - 1 THEN
      DESAT.HIGH = (MA2 - (2 * HIGHO2 - 1)) /
             (1 - (2 * HIGHO2 - 1))
ELSE
      DESAT.HIGH = 0
END IF REM Fuzzify rate into fuzzy set ARTifact
REM Triangular membership functions IF ABSRATE > testRATE.HIGH THEN
      RATE.HIGH = 1
      RATE.MEDIUM = 0
      RATE. LOW = 0
ELSEIF ABSRATE > testRATE.MEDIUM THEN
      RATE.HIGH = (ABSRATE - testRATE.MEDIUM) /
            (testRATE.HIGH - testRATE.MED)
      RATE.MEDIUM = FNFZNOT (RATE.HIGH)
      RATE.LOW = 0
ELSE
      RATE.HIGH = 0
      RATE.MEDIUM = (ABSRATE - testRATE.LOW) /
            (testRATE.MEDIUM)
      RATE.LOW = FNFZNOT (RATE.MEDIUM)
```

Fig. 2 F
Computer Program Listing

```
END IF

REM Existence of artifact depends on last and current status
REM Rule:    if (old artifact and desat) or (rate HIGH) then
REM              current artifact ARTIFACT.YES = FNFZOR (RATE.HIGH, FNFZAND
    (oldARTIFACT.YES, DESAT.YES))
ARTIFACT.NO = FNFZNOT (ARTIFACT.YES)

REM Rule: if rate medium then give artifact warning only

WARN = RATE.MEDIUM
IF WARN > .5 THEN
    SOUND 256, .5
    CIRCLE (I, RATE2 * MPY + .5), 3, 1
    CIRCLE (I, SAO22), 3, 1
    REM Reset moving average
    MA2 = SAO22
END IF REM Rule: if artifact then take action IF ARTIFACT.YES > .5 THEN
    REM Reset moving average
    MA2 = SAO22
    LINECOLOR = 1
    REM CIRCLE (I, SAO22), 3
    SOUND 256, .5
ELSE
    LINECOLOR = 3
END IF REM Now O2 level tests
REM Rule:    if O2 level high then give warning
REM              else restore warning line color IF DESAT.HIGH > .5 THEN
LINECOLOR = 1
    IF I MOD 50 = 0 AND SOUNDHI$ = "Y" THEN SOUND 440, .5
ELSEIF ARTIFACT.NO > .5 THEN
    LINECOLOR = 3
END IF REM Now if in desaturation, be sure we are not in an artifact
REM Rule:    if O2 level in desaturation and no artifact then
                reset confidence in DESAT.YES

DESAT.YES = FNFZAND (DESAT.YES, ARTIFACT.NO)
```

Fig. 2 G
Computer Program Listing

REM Rule: if still in desaturation, then -- (consequence more rules)

IF DESAT.YES > .5 THEN
    REM If desaturation, make sure it has held up long enough     REM Rule:    if not previously desaturated set desat time to zero,
    REM            ELSE INCREMENT DESAT TIME
    IF oldDESAT.NO > .5 THEN
        TDESAT = 0
    ELSE
        TDESAT = TDESAT + DX
    END IF     REM Rule: if desat time > 2 seconds then issue warning
    IF TDESAT > 20 THEN
        REM Signal desaturation
        LINECOLOR = 2
        REM Sound alternating tones
        IF TDESAT MOD 40 < 20 THEN
            SOUND 602, .25
        ELSE
            SOUND 512, .25
        END IF
    END IF: REM End if desat time > 2 seconds
END IF: REM End if now in desaturation REM Reset old values
SAO21 = SAO22
MA1 = MA2
RATE1 = RATE2
oldDESAT.YES = DESAT.YES
oldDESAT.NO = DESAT.NO
oldARTIFACT.YES = ARTIFACT.YES
oldARTIFACT.NO = ARTIFACT.NO

NEXT I

REM If key pressed, honor it:
REM Q stop; P pause; U up slope: D down slope: H = toggle high warn sound A$ = UCASE$ (INKEY$)
IF A$ = "Q" THEN
    GOTO FINISH
ELSEIF A$ = "P" THEN
    DO: LOOP WHILE INKEY$ = ""
ELSEIF A$ = "U" THEN
    testRATE.MEDIUM = testRATE.MEDIUM * 1.2
    testRATE.HIGH = testRATE.HIGH * 1.2
ELSEIF A$ = "D" THEN

Fig. 2H
Computer Program Listing

```
        testRATE.MEDIUM = testRATE.MEDIUM / 1.2
        testRATE.HIGH = testRATE.HIGH / 1.2
    ELSEIF A$ = "H" THEN
        IF SOUNDHI$ = "Y" THEN
            SOUNDHI$ = "N"
        ELSE
            SOUNDHI$ = "Y"
        END IF
    END IF

CLS
NEXT FRAME

FINISH:
DO: LOOP WHILE INKEY$ = ""
SCREEN 0
WIDTH 80
PRINT "Plotted"; 300 * FRAME / PIX + I / PIX; "points."
END

NOFILE:
DO: LOOP WHILE INKEY$ = ""
SCREEN 0
WIDTH 80
PRINT "END OF DATA"
END
```

FUZZY LOGIC ALARM SYSTEM FOR PULSE OXIMETERS

BACKGROUND—FIELD OF INVENTION

This invention relates to oximetry and, more particularly, to alarm systems used in pulse oximeters.

BACKGROUND—DESCRIPTION OF PRIOR ART

Non-invasive pulse oximeters are being used by more than 600 intensive care nurseries in the United States, for more than 80% of mechanically ventilated infants. Pulse oximeters are just one of many technological devices being used in intensive care nurseries in an attempt to measure accurately and monitor carefully the level of oxygenation.

Since the publication, in 1954, of the association of retrolental fibroplasia in premature infants with high concentrations of inspired oxygen, efforts have been made to develop accurate methods of measurement of oxygenation in infants. Although excessive arterial oxygen has been associated with retrolental fibroplasia, changes in pulmonary epithelium, and bronchopulmonary dysplasia, inadequate oxygenation has been associated with spastic diplegia, delay in tissue growth and function, and increased pulmonary vascular resistance. Bronchopulmonary dysplasia is the major cause of significant morbidity among survivors of respiratory distress syndrome. Each year in the United States up to 20% of low birthweight infants and others who survive intensive nursery care have long-term sequelae of neurodevelopmental disorders, blindness, or chronic respiratory problems. Health care providers seek to use monitors which will alert them when an infant is over or under-oxygenated. One such device is the pulse oximeter.

The pulse oximeter is a spectrophotometric device which measures oxygen saturation by differentiating light absorbances of reduced and oxygenated hemoglobin during arterial pulsations. It is an attractive monitor for neonatal and pediatric health care providers because it measures oxygenation non-invasively and continuously.

The ability to measure spectroscopically oxygen saturation by the change in transmitted light was first discovered in 1875 by Karl von Vierordt. U.S. Pat. No. 3,638,640 to Robert Shaw (1972) shows a self-calibrating, 8 wavelength ear oximeter, which was used in physiology and cardiac catheterization laboratories. There was no alarm system on this early device.

The first pulse oximeter was invented in 1972 in Tokyo, Japan, by Takuo Aoyagi. In U.S. Pat. No. 4,407,290, Wilber (1983) described how light pulses at two different wavelengths are applied to an earlobe. He did not describe an alarm system. U.S. Pat. No. 4,167,331 (Nielson, 1979) disclosed a pulse transmittance oximeter based upon the principle that the absorption of light by a material is directly proportional to the logarithm of the light intensity after having been attenuated by the absorber, according to the Beer-Lambert law. These principles are the basis for the pulse oximeters that are used clinically, today. Although readings of oxygen saturation and heart rate output leads are shown and described in Neilson's patent, an alarm system is not.

U.S. Pat. No. 4,453,218 (Sperinde et al., 1984) discloses a signal filter method and apparatus for removing portions of a signal indicative of erroneous data resulting from reflective characteristics of blood vessel walls. This invention is particularly suited for use with catheter-type oximeters that are inserted into blood vessels. This patent shows an alarm system but describes its design and function only as an output circuit which generates an audio alarm tone.

In U.S. Pat. No. 4,800,495, Smith (1989) describes a new signal processing technique to improve the accuracy of the pulse oximeter. The positive peak, negative peak, and period of the signal are identified by searching for a sustained positive sloping region of the signal. The peaks are then compared to waveform templates to determine acceptable values for amplitude and intervals. In Smith's patent, the alarm is shown and mentioned, but its design and function are not described.

Although the reliability of the pulse oximeter is well established in adult, pediatric, and neonatal populations, in all of the reliability studies the correlating arterial blood gases were obtained while the subjects were quiet and when the pulse rate measured by the oximeter was equal to that measured by the cardiac monitor. In the intensive care nursery, all but paralyzed or moribund infants move around, causing interference to the pulsations sensed by the pulse oximeter, which causes the alarm to sound falsely.

Motion artifact has been estimated to occur 12–29% of the time, resulting in poor specificity. This frequent, excessive sounding of alarms may be overstimulating for infants and parents and dangerous if it causes a "Cry Wolf" response among nurses and other caretakers, which could result in unrecognized hypoxia or hyperoxia.

BRIEF SUMMARY OF THE INVENTION

The invention discloses a new alarm system for a pulse oximeter used for newborns and infants which will differentiate false alarms, caused by artifact, from true alarms. The method used in the design of this alarm is based on a new branch of mathematics, fuzzy systems theory, popularly called fuzzy logic.

We developed a fuzzy logic computer prototype alarm system using fuzzy sets of oxygen saturation, rate of change of oxygen saturation, and artifact. We have demonstrated that the fuzzy logic pulse oximeter alarm system has improved specificity, without compromising sensitivity, when compared with a conventional pulse oximeter alarm system.

Thirty-eight infants with a mean (range) study weight of 1495 g (470-3390) were enrolled in the study. Oxygen saturation signals were collected for 1 hour per infant on a strip chart recorder and saved on a computer. Reference signals were simultaneously recorded from a second pulse oximeter and transcutaneous oxygen monitor. The prototype versus conventional alarms were compared to the reference for 919 alarm events. If an alarm persisted, it was analyzed each 30 second interval was considered an independent event. "Hypoxemia" was initially defined as transcutaneous partial pressure of oxygen of <40 torr and oxygen saturation of <85% for the reference.

The prototype alarm system had 34% fewer false positive alarms and did not miss any true alarms. The prototype fuzzy logic alarm system has equivalent sensitivity and improved specificity versus the conventional alarm system. When used to monitor oxygenation in infants, this system with fewer false alarms may decrease the "Cry Wolf" response among caretakers.

BRIEF DESCRIPTION OF THE DRAWING AND LISTING

FIG. 2A is the execution directions for the fuzzy logic alarm system computer program.

DETAILED DESCRIPTION OF THE DRAWINGS

An understanding of the relevant theory begins with a discussion of fuzzy logic and its appropriate application to this device. Fuzzy logic has become a generic term for fuzzy systems theory, an new and unconventional branch of mathematics. It has its roots in the introduction of quantum mechanics, with its inherent ambiguities, and in the work done on fuzzy systems by Lukaciewicz in the 1920's. In 1965, Lotfi Zadeh realized that many systems dealing with uncertainties, ambiguities and contradictions could not be well described by conventional mathematics, so he developed the theory of fuzzy systems, including the theories of fuzzy sets, fuzzy numbers and fuzzy logic. At first received with considerable hostility in this country, fuzzy systems theory has had remarkable success in Japan, especially in the area of fuzzy process control, and has received increasing interest in this country in the past few years.

Fuzzy logic has been applied most successfully to processes involving quantities which most humans would describe in sets of linguistic terms such as {SMALL, MEDIUM, LARGE} or {SLOW, MODERATE, FAST}, with a degree of confidence from 0 to 1 attached to each linguistic term. The use of these terms permits rule-based reasoning which closely approximates actual human reasoning processes. Fuzzy logic is particularly suitable for describing human decision-making processes which cannot be precisely described in conventional mathematical terms. For reasoning purposes, numeric variables are mapped onto a fuzzy set of linguisic variables by a set of membership functions which permit replacing the original numeric measurement by confidences attached to each linguistic term. For example, a height measurement of 5.98 feet might be replaced by the linguistic terms SHORT (confidence 0), MEDIUM (confidence 0.3), TALL (confidence 1.0), VERY_TALL (confidence 0.75). Rules could then be written such as IF A MAN IS TALL AND VERY_HEAVY AND ATHLETIC THEN HE MIGHT BE A FOOTBALL_ PLAYER. The application of this rule to a particular man using fuzzy logic would produce the confidence that the term FOOTBALL_PLAYER might be applicable to that man. Conventional Aristotelian logic does not permit this type of reasoning.

The fuzzy logic program includes fuzzy sets of linguistic input and output variables, and components of the decision process including a set of rules which yield a resulting decision set. Domain experts were consulted to determine the membership functions for the input variables. The result of the fuzzy logic programming is a decision set, e.g. different types of alarms for artifact, oxygen desaturation, or oxygen oversaturation.

After viewing hundreds of oxygen saturation tracings, one of the inventors identified characteristic patterns of oxygen saturation signals that were attributed to artifacts compared to true signals. Because the pulse oximeter alarm emulates a human decision process with ambiguities, and patterns of change of the variables are describable, the application of fuzzy logic was thought to be appropriate to develop a new alarm system.

Input variables and membership functions for the fuzzy logic program were identified, resulting in the fuzzy sets entitled oxygen saturation, rate of change of oxygen saturation, and artifact. Another input variable of rate of change of heart rate, and its corresponding membership functions, will be added. As shown in FIG. 2A, the members of the fuzzy set of rate of change are high, medium, and low. The members of the fuzzy set of oxygen saturation are yes, no, and high. The members of the fuzzy set of artifact are yes and no. For programming purposes, there are also the fuzzy set of old desaturation with the members yes and no, and the fuzzy set of old artifact with the members yes and no.

Figure 1:
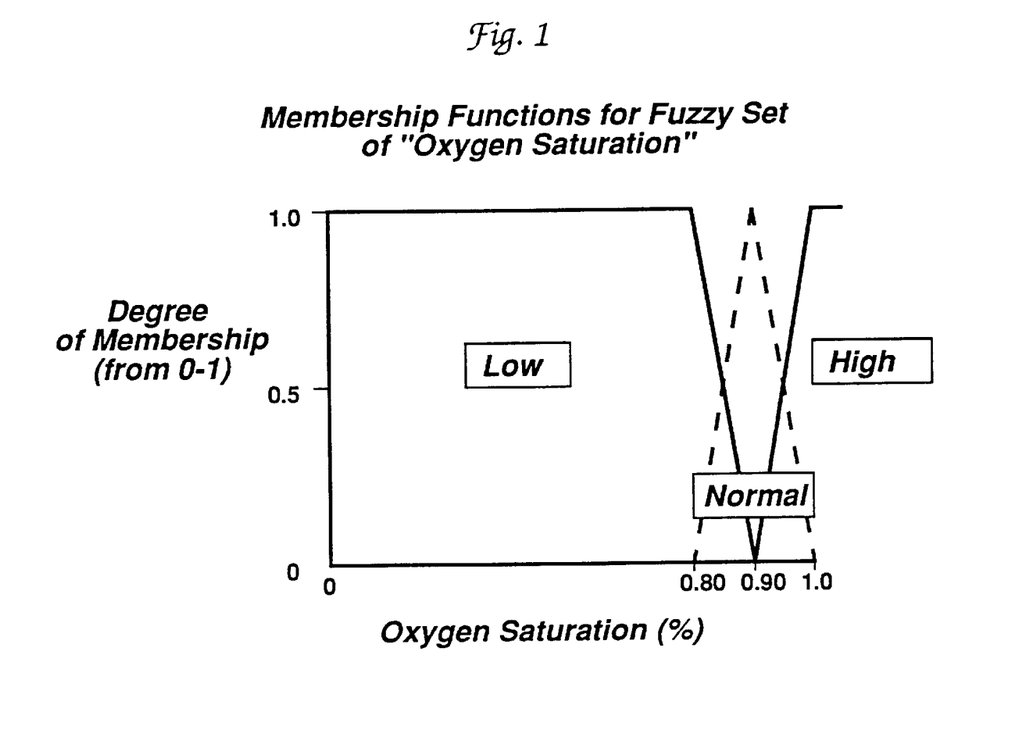
FIG. 1 is a graphical illustration of the fuzzy set of oxygen saturation.

The input variables were obtained as voltages from 0–1 volts, smapled and converted to digital form. Discussions among investigators resulted in preliminary estimates of the membership functions, which map an input numeric value onto the degree of membership of a linguistic variable within the fuzzy sets. The membership functions for the fuzzy set describing oxygen saturation is shown in FIG. 1. Membership functions for the fuzzy set RATE are similar, and typical values defining these membership functions are given in FIG. 2A, instructions for running the prototype computer alarm program itself. The actions of the decision set include identification of high oxygen, momentary artifact, continuous artifact, and desaturation. These actions each result in a characteristic color of the signal tracing on the graph and pulses of sound in Hertz for the appropriate type of alarm.

The tracing of the signal changes color and the quality of the sound of the alarm changes according to each situation, as indicated in FIG. 2A. High oxygen saturation results in a blue graphical tracing and pulses of sound at 440 Hertz. Momentary artifact results in a small blue circle drawn on the graphical tracing, and a short pulse of sound at 256 Hertz. Continuous artifact results in a blue tracing, and a sound at 256 Hertz. Oxygen desaturation results in a red tracing and a sound alternating between 512 and 602 Hertz. When the oxygen saturation is within normal limits, the tracing has a characteristic color of white, and no alarm sounds. The colors of the tracing and quality of the sound of the alarm in Hertz can be changed in the program.

Figure 2B:
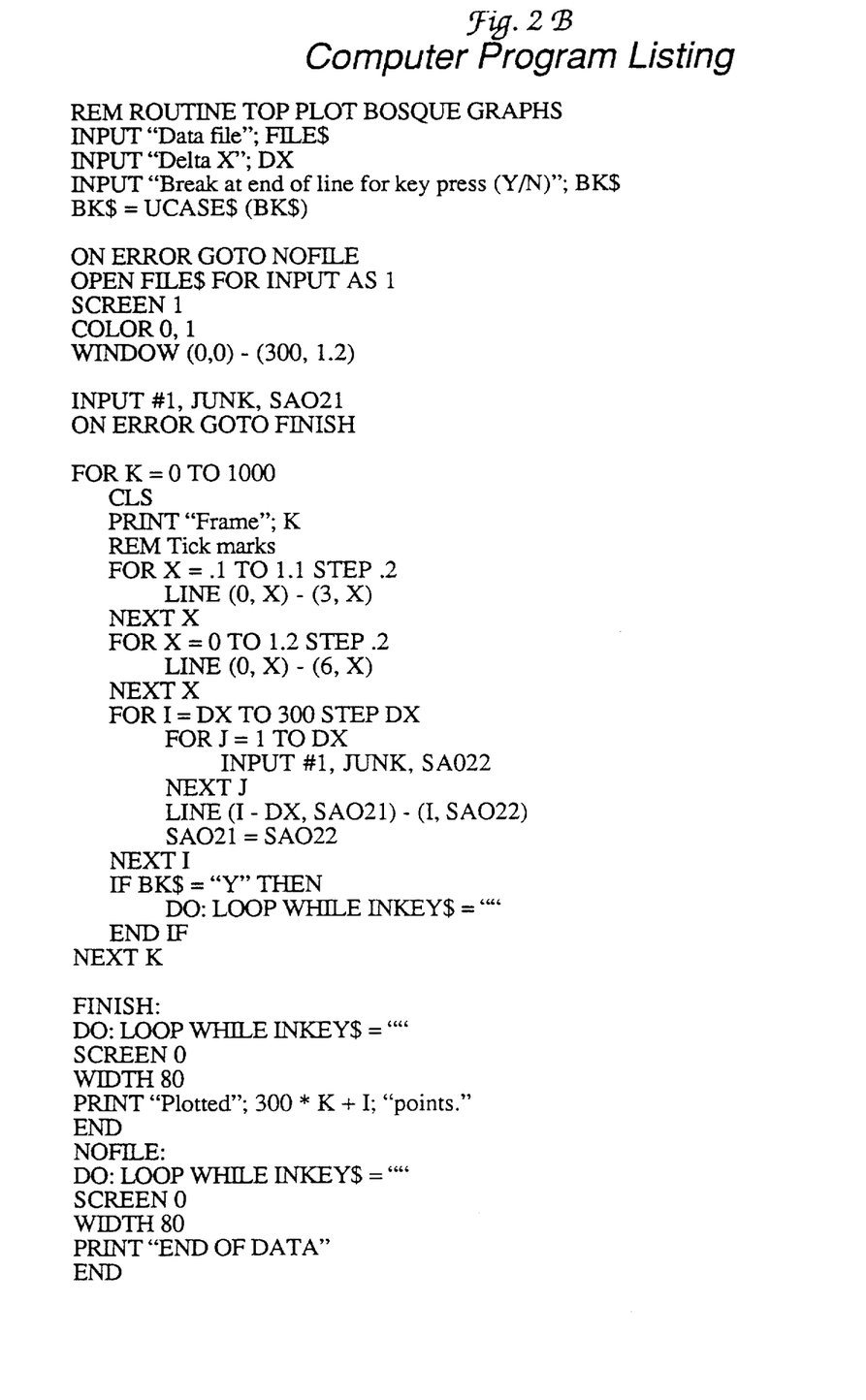
FIG. 2B is the fuzzy logic alarm system computer program commands for the plotting of the graphs.
Figure 2C:
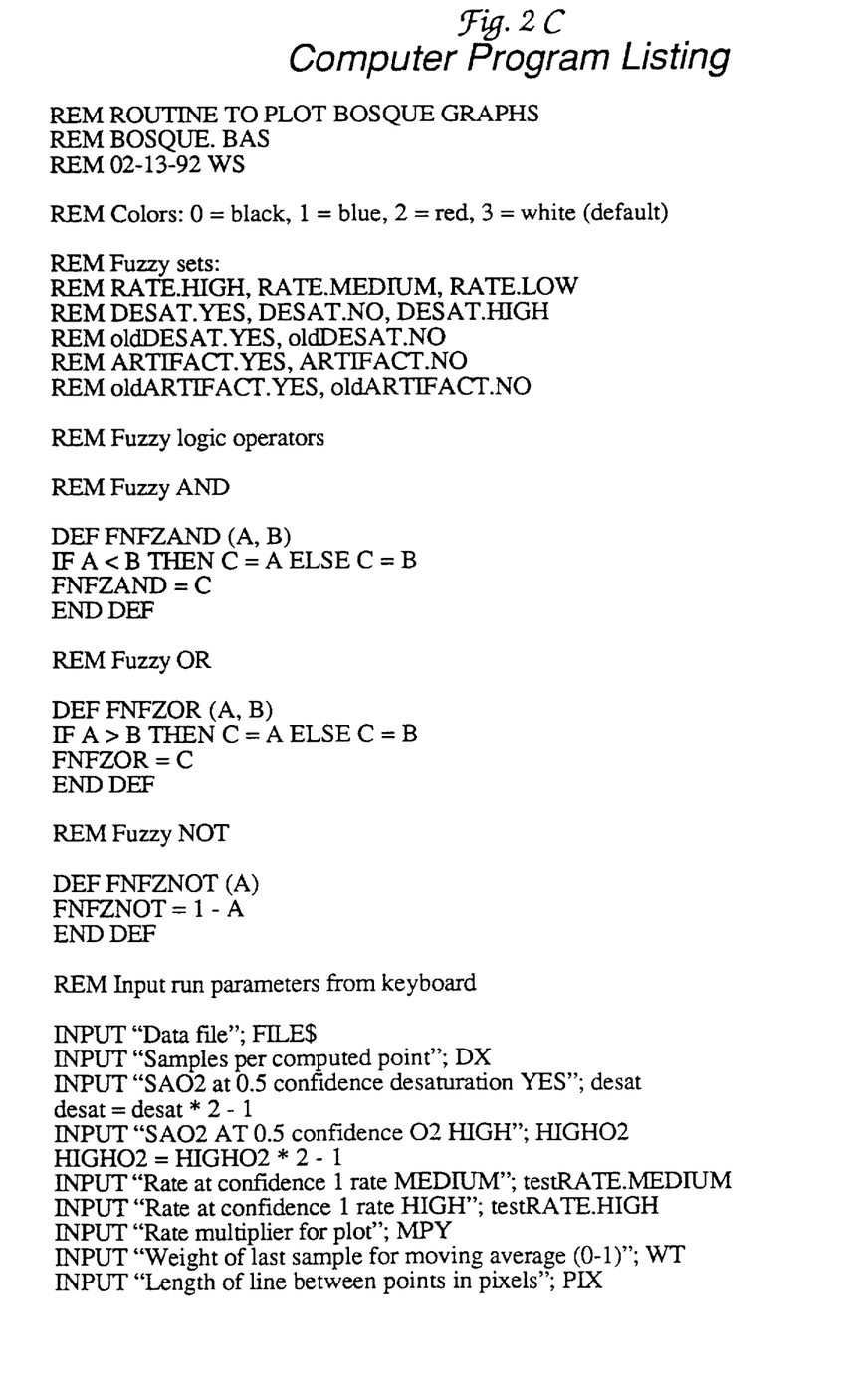
FIGS. 2C to 2H is the computer program listing for the fuzzy logic alarm system.
Figure 2D:
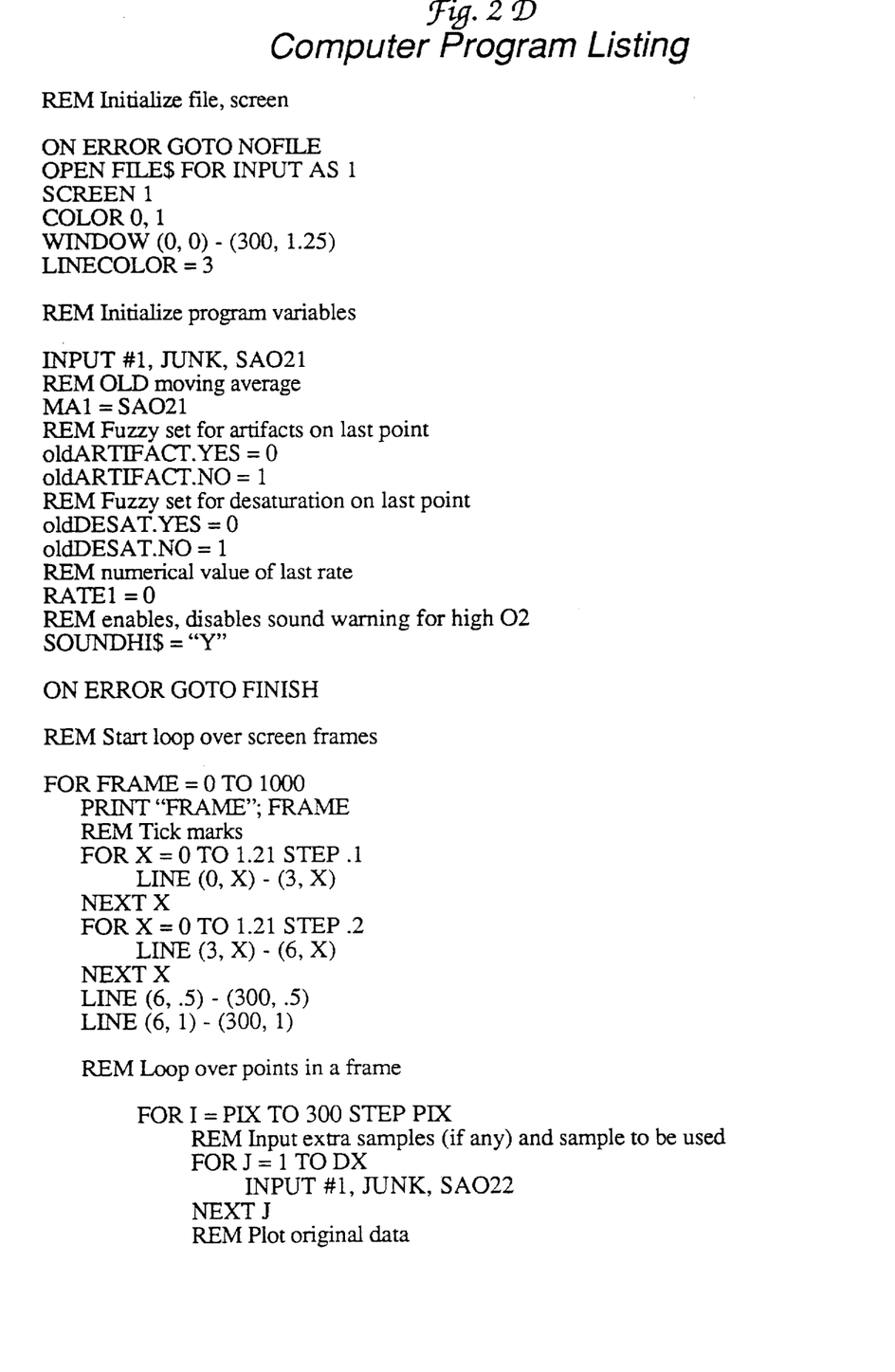
Figure 2E:
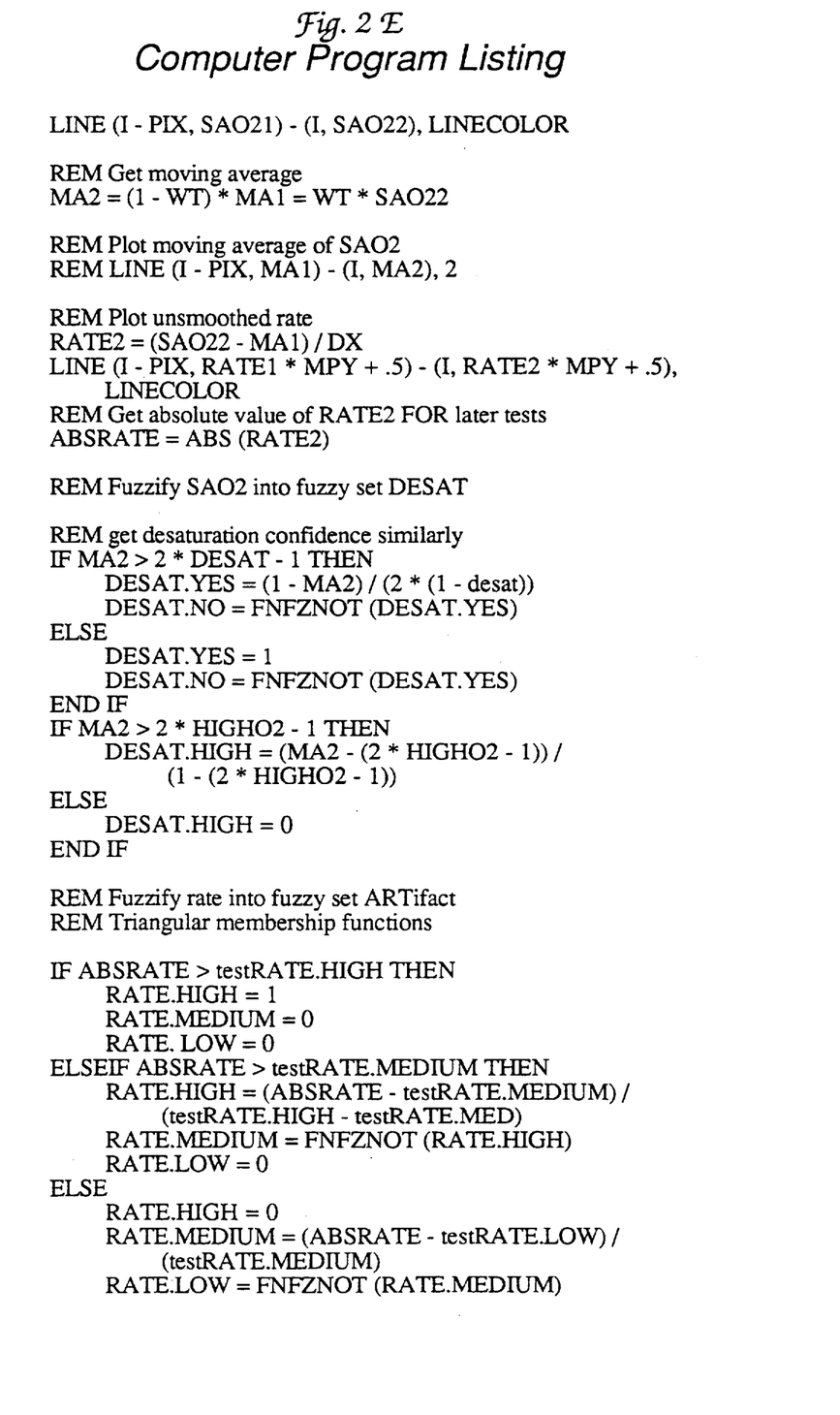
Figure 2F:
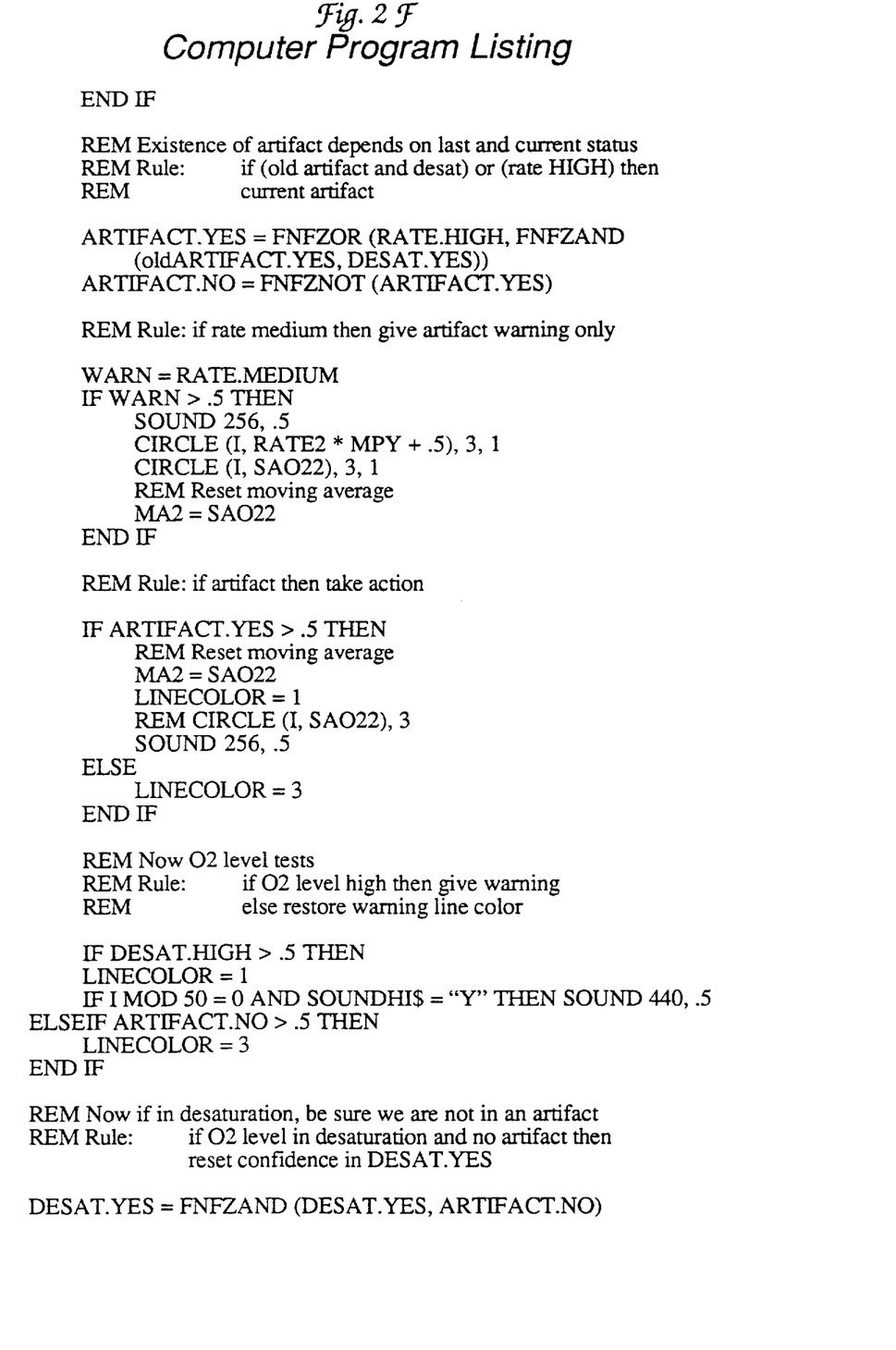
Figure 2G:
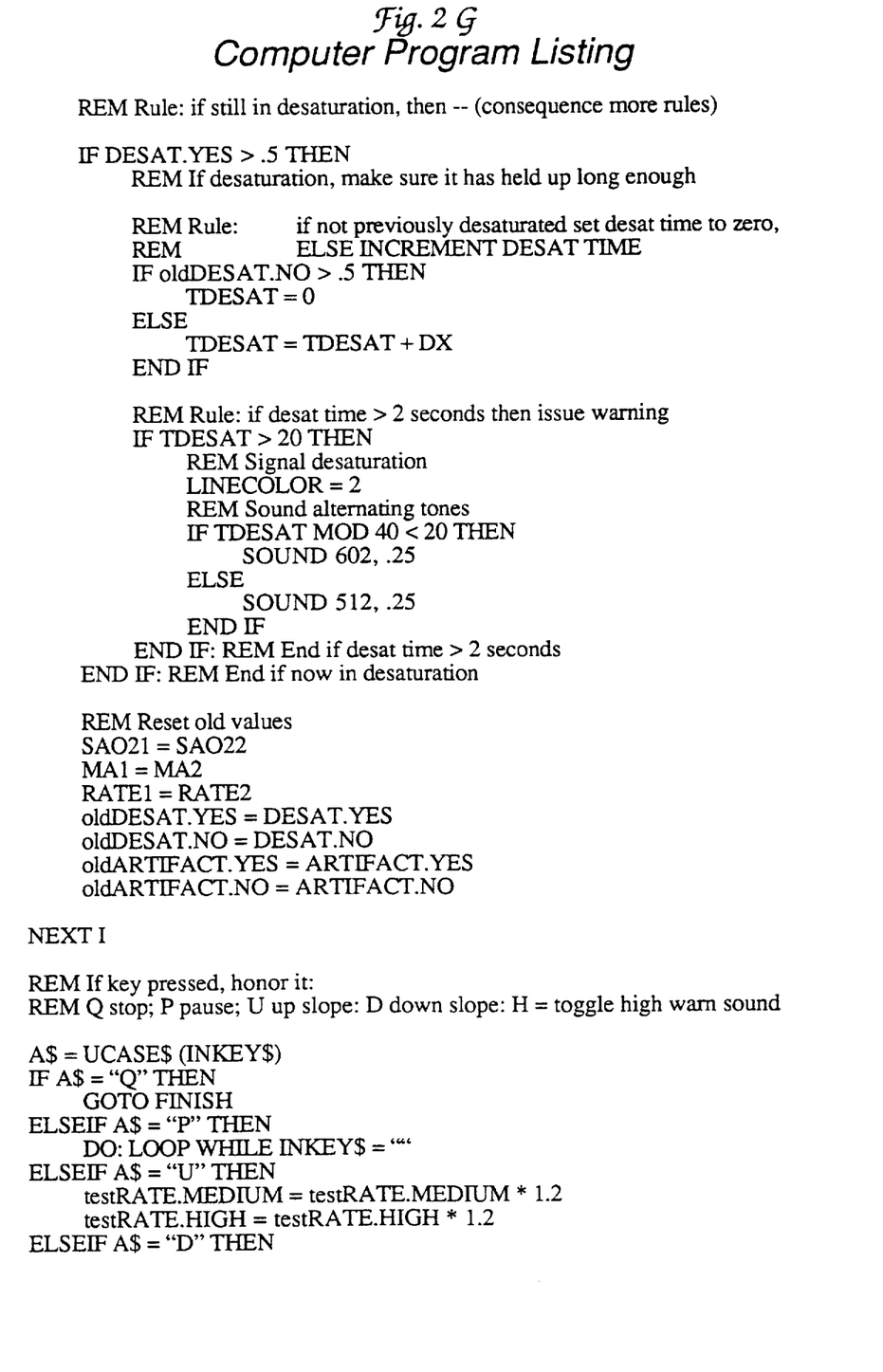
Figure 2H:
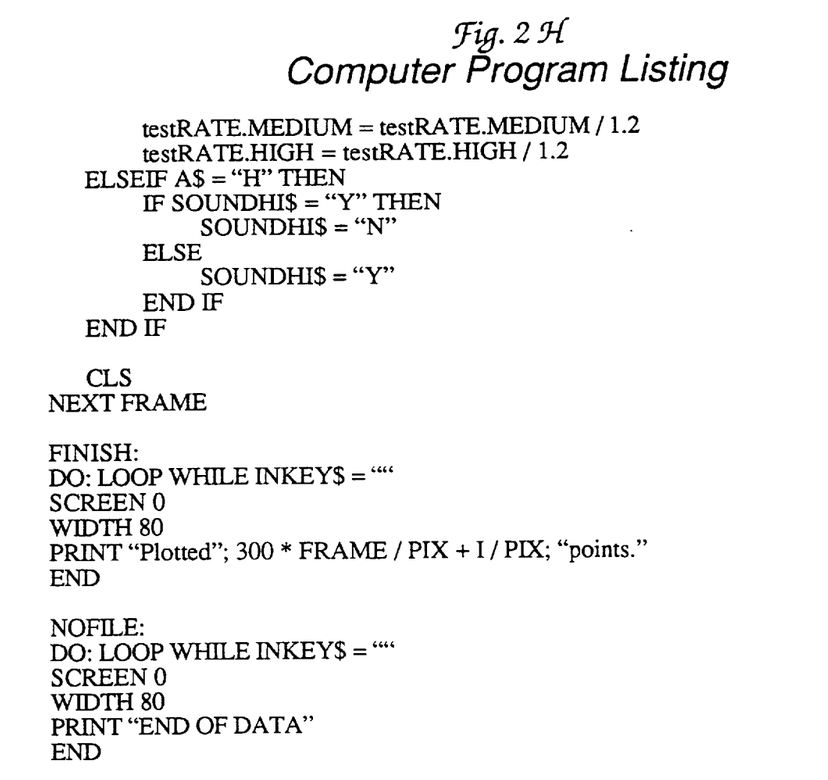

There are run-time options at the end of a frame, given in FIG. 2A, allowing the operator to pause, quit, or adjust the level of fuzzification, altering the sensitivity to artifact. A program listing for simply plotting the input signals is shown in FIG. 2B. The time length was 30 seconds for each screen frame of the computer data in the fuzzy logic alarm system program. The program functions for determining the union, intersection and negation of fuzzy sets are shown in FIGS. 2C; the complete alarm detection program is shown in FIGS. 2C to 2H.

Figure 3:
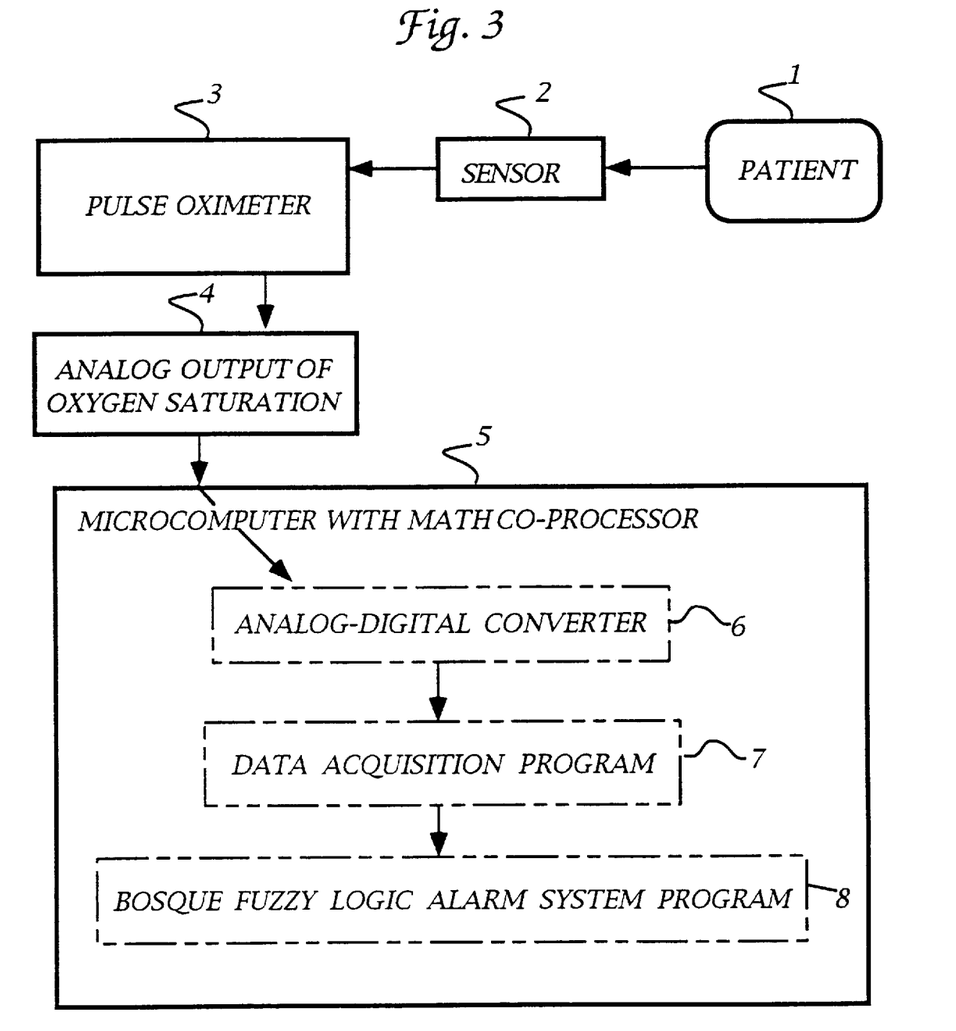
FIG. 3 is a block diagram of the prototype fuzzy logic alarm system including a patient, sensor, pulse oximeter, analog output of the oxygen saturation signal, a microcomputer with a math co-processor, analog-digital converter, data acquisition program, and the fuzzy logic alarm system program.

As shown in FIG. 3, the patient (1) has a sensor (2), typically wrapped around a hand or foot. The pulse oximeter oxygen saturation signal from 0–1 volt (3) is taken from an analog output port through a cable with a phone plug (4). The oxygen saturation signal is then entered into a data acquisition program (7) on a microcomputer with a math co-processor (5) through an analog-digital converter (6). The fuzzy logic alarm system program, written in Quick Basic 4.5, by Microsoft_ (8), is applied to the data and differentiates the artifact from the true signals. A decision set determines which type of alarm to sound, including artifact, oxygen desaturation, oxygen oversaturation.

The fuzzy logic alarm system computer program, as shown in FIGS. 2C to 2H, may be loaded into the memory of a microcomputer, as shown in FIG. 3, or (in machine language) may be transcribed into Read Only Memory (ROM) for use with a microcomputer, or can be converted into special-purpose VLSI circuitry on a fuzzy logic computer chip. The fuzzy logic computer chip may be inserted directly into a pulse oximeter.

The advantage of using the fuzzy logic alarm system for a pulse oximeter is that there will be at least 34% fewer false alarms. An alarm will still sound for an artifact event, as one will for other events including oxygen desaturation or oxygen oversaturation. An artifact alarm will alert the caretaker to the need to visually monitor the infant because the pulse oximeter is not accurately sensing the pulse. An alarm indicating oxygen desaturation or oversaturation will indicate the need for intervention on the part of the caretaker. Alarms which better reflect the actual situation will decrease the amount of false alarms, improve specificity of the alarm system, and may decrease the potential "Cry Wolf" response of the caretaker, which exists now.

While the references have been described with reference to a preferred embodiment, it is to be clearly understood by those skilled in the art that the invention is not limited thereto, and that the scope of the invention is to be interpreted only in conjunction with the following claims.

We claim:

1. A method for differentiating artifact from true oxygen saturation signals using pulse oximetry and a computer system comprising:

a) generating an oxygen saturation signal which may correspond to the oxygen saturation level in a subject's blood;

b) storing the oxygen saturation signal in a data storage area of the computer system;

c) applying a fuzzy logic alarm system computer program to the oxygen saturation signal stored in the computer system in order to determine whether the stored oxygen saturation signal is a true signal actually corresponding to the oxygen saturation level in a subject's blood or an artifact, the fuzzy logic alarm system computer program comprising fuzzy sets; linguistic variables; membership functions; confidence values; rules and constraints; membership functions for unions of fuzzy sets; membership functions for triangulations of fuzzy sets; and decision sets; and d) generating a detectable indicator signal based upon the determination made when applying the fuzzy logic alarm system computer program to the stored oxygen saturation signal to indicate a state of the oxygen saturation signal;

wherein one of the fuzzy sets includes rate of change of heart rate data.

2. The method of claim 1 wherein the detectable indicator signal indicates one of the following states: momentary artifact; continuous artifact; normal oxygen saturation; oxygen desaturation; and, oxygen oversaturation.

3. The method of claim 1 wherein between the generating and storing the oxygen saturation signal steps, the method comprises the further step of converting the oxygen saturation signal to a digital data signal.

4. A method for differentiating artifact from true oxygen saturation signals using pulse oximetry and a computer system, comprising:

a) generating an oxygen saturation signal which may correspond to the oxygen saturation level in a subject's blood;

b) converting the oxygen saturation signal to a data signal;

c) storing the data signal in a data storage area of the computer system;

d) applying a fuzzy logic alarm system computer program to the data signal stored in the data storage area of the computer system in order to determine whether the data signal is a true signal actually corresponding to the oxygen saturation level in a subject's blood or an artifact, the fuzzy logic alarm system computer program comprising fuzzy sets; linguistic variables; membership functions; confidence values; rules and constraints; membership functions for unions of fuzzy sets; membership functions for triangulations of fuzzy sets; and decision sets; and, e) generating a detectable indicator signal based upon the determination made when applying the fuzzy logic alarm system computer program to the stored data signal to indicate a state of the data signal; wherein one of the fuzzy sets includes rate of change of heart rate data.

5. The method of claim 4 wherein the detectable indicator signal indicates one of the following states: momentary artifact; continuous artifact; normal oxygen saturation; oxygen desaturation; and, oxygen oversaturation.

6. An apparatus for differentiating artifact from true oxygen saturation signals using a computer system with data storage and data processing capabilities, comprising:

a) means for generating an oxygen saturation signal which may correspond to the oxygen saturation level in a subject's blood;

b) means for storing the oxygen saturation signal in a data storage area of the computer system;

c) means for applying a fuzzy logic alarm system computer program to the oxygen saturation signal stored in the data storage area of the computer system in order to determine whether the stored oxygen saturation signal is a true signal actually corresponding to the oxygen saturation level in a subject's blood or an artifact, the fuzzy logic alarm system computer program comprising fuzzy sets; linguistic variables; membership functions; confidence values; rules and constraints; membership functions for unions of fuzzy sets; membership functions for triangulations of fuzzy sets; and decision sets; and, d) means for generating a detectable indicator signal based upon the determination made when applying the fuzzy logic alarm system computer program to the stored oxygen saturation signal to indicate a state of the oxygen saturation signal;

wherein one of the fuzzy sets includes rate of change of heart rate data.

7. The apparatus of claim 6 wherein the detectable indicator signal means indicates one of the following states: momentary artifact; continuous artifact; normal oxygen saturation; oxygen desaturation; and, oxygen oversaturation.

8. An apparatus for differentiating artifact from true oxygen saturation signals using a computer system with data storage and data processing capabilities, comprising:

a) means for generating an oxygen saturation signal which may correspond to the oxygen saturation level in a subject's blood;

b) means for converting the oxygen saturation signal to a data signal;

c) means for storing the data signal in a data storage area of the computer system;

d) means for applying a fuzzy logic alarm system computer program to the data signal stored in the data storage area of the computer system in order to determine whether the data signal is a true signal actually corresponding to the oxygen saturation level in a subject's blood or an artifact, the fuzzy logic alarm system computer program comprising fuzzy sets; linguistic variables; membership functions; confidence values; rules and constraints; membership functions for unions of fuzzy sets; membership functions for triangulations of fuzzy sets; and decision sets; and, e) means for generating a detectable indicator signal based upon the determination made when applying the fuzzy logic alarm system computer program to the stored data signal to indicate a state of the data signal;

wherein one of the fuzzy sets includes rate of change of heart rate data.

9. The apparatus of claim 8 wherein the detectable indicator signal means indicates one of the following states: momentary artifact; continuous artifact; normal oxygen saturation; oxygen desaturation; and, oxygen oversaturation.

10. An apparatus for differentiating artifact from true oxygen saturation signals using a pulse oximeter with data storage and data processing capabilities, comprising:

a) a pulse oximeter for generating an oxygen saturation signal which may correspond to the oxygen saturation level in a subject's blood;

b) means for storing the oxygen saturation signal in a data storage area of the pulse oximeter;

c) means for applying a fuzzy logic alarm system computer program to the stored oxygen saturation signal stored in the pulse oximeter data storage area in order to determine whether the stored oxygen saturation signal is a true signal actually corresponding to the oxygen saturation level in a subject's blood or an artifact, the fuzzy logic alarm system computer program comprising fuzzy sets; linguistic variables; membership functions; confidence values; rules and constraints; membership functions for unions of fuzzy sets; membership functions for triangulations of fuzzy sets; and decision sets; and, d) means for generating a detectable indicator signal based upon the determination made when applying the fuzzy logic alarm system computer program to the stored oxygen saturation signal to indicate a state of the oxygen saturation signal;

wherein one of the fuzzy sets includes rate of change of heart rate data.

11. The apparatus of claim 10 wherein the fuzzy logic alarm system computer program is stored in a fuzzy logic computer chip contained within the pulse oximeter.

12. The apparatus of claim 10 wherein the detectable indicator signal means indicates one of the following states: momentary artifact; continuous artifact; normal oxygen saturation; oxygen desaturation; and, oxygen oversaturation.

13. An apparatus for differentiating artifact from true oxygen saturation signals using a pulse oximeter and a computer system with data storage and data processing capabilities, comprising:

a) a pulse oximeter for generating an oxygen saturation signal which may correspond to the oxygen saturation level in a subject's blood;

b) means for storing the oxygen saturation signal in a data storage area of the computer system;

c) means for applying a fuzzy logic alarm system computer program to the stored oxygen saturation signal in order to determine whether the stored oxygen saturation signal is a true signal actually corresponding to the oxygen saturation level in a subject's blood or an artifact, the fuzzy logic alarm system computer program comprising fuzzy sets; linguistic variables; membership functions; confidence values; rules and constraints; membership functions for unions of fuzzy sets; membership functions for triangulations of fuzzy sets; and decision sets; and, d) means for generating a detectable indicator signal in the pulse oximeter based upon the determination made when applying the fuzzy logic alarm system computer program to the stored oxygen saturation signal to indicate a state of the oxygen saturation signal;

wherein one of the fuzzy sets includes rate of change of heart rate data.

14. The apparatus of claim 13 wherein the detectable indicator signal means indicates one of the following states: momentary artifact; continuous artifact; normal oxygen saturation; oxygen desaturation; and, oxygen oversaturation.

15. An apparatus for differentiating artifact from true oxygen saturation signals using a pulse oximeter and a computer system with data storage and data processing capabilities, comprising:

a) a pulse oximeter for generating an oxygen saturation signal which may correspond to the oxygen saturation level in a subject's blood;

b) means for storing the oxygen saturation signal in a data storage area of the computer system;

c) means for applying a fuzzy logic alarm system computer program to the stored oxygen saturation signal in order to determine whether the stored oxygen saturation signal is a true signal actually corresponding to the oxygen saturation level in a subject's blood or an artifact, the fuzzy logic alarm system computer program comprising fuzzy sets; linguistic variables; membership functions; confidence values; rules and constraints; membership functions for unions of fuzzy sets; membership functions for triangulations of fuzzy sets; and decision sets; and, d) means for generating a detectable indicator signal in the computer system based upon the determination made when applying the fuzzy logic alarm system computer program to the stored oxygen saturation signal to indicate a state of the oxygen saturation signal;

wherein one of the fuzzy sets includes rate of change of heart rate data.

16. The apparatus of claim 15 wherein the detectable indicator signal means indicates one of the following states: momentary artifact; continuous artifact; normal oxygen saturation; oxygen desaturation; and, oxygen oversaturation.

* * * * *